United States Patent
Wang et al.

(10) Patent No.: US 10,247,686 B2
(45) Date of Patent: Apr. 2, 2019

(54) COMPRESSION HEAT-GENERATION DETECTOR AND METHOD THEREFOR

(71) Applicant: EVE RUBBER INSTITUTE CO., LTD., Qingdao, Shandong (CN)

(72) Inventors: Meng-Jiao Wang, Bedford, MA (US); Deying Dai, Shandong (CN); Pengzhang Wu, Shandong (CN); Shijie Liu, Shandong (CN)

(73) Assignee: EVE RUBBER INSTITUTE CO., LTD., Qingdao, Shandong (CN)

( * ) Notice: Subject to any disclaimer, the term of this patent is extended or adjusted under 35 U.S.C. 154(b) by 157 days.

(21) Appl. No.: 15/317,893

(22) PCT Filed: Jul. 22, 2014

(86) PCT No.: PCT/CN2014/082684
§ 371 (c)(1),
(2) Date: Dec. 9, 2016

(87) PCT Pub. No.: WO2015/192437
PCT Pub. Date: Dec. 23, 2015

(65) Prior Publication Data
US 2017/0131225 A1    May 11, 2017

(30) Foreign Application Priority Data
Jun. 16, 2014    (CN) .......................... 2014 1 0268592

(51) Int. Cl.
*G01K 1/00*    (2006.01)
*G01K 13/00*    (2006.01)
(Continued)

(52) U.S. Cl.
CPC ............. *G01N 25/20* (2013.01); *G01K 17/00* (2013.01); *G01N 3/08* (2013.01); *G01N 33/445* (2013.01)

(58) Field of Classification Search
USPC ................................................ 374/142, 208
See application file for complete search history.

(56) References Cited

U.S. PATENT DOCUMENTS 3,531,996 A    10/1970    Harris et al.
5,959,215 A    9/1999    Ono et al.

FOREIGN PATENT DOCUMENTS

CN    1793918 A    6/2006
JP    H6-281606 A    10/1994
(Continued)

OTHER PUBLICATIONS

International Search Report dated Mar. 17, 2015 issued in corresponding International Application No. PCT/CN2014/082684.
(Continued)

*Primary Examiner* — Mirellys Jagan
(74) *Attorney, Agent, or Firm* — Nath, Goldberg & Meyer; Jerald L. Meyer

(57) ABSTRACT

A compression heat-generation detector and a method therefor include one set or multi-sets of detecting units. The detecting unit includes a vertical compression device, a vertical compensation device and a synchronization device for a core center temperature sensor. The vertical compression device and the vertical compensation device are respectively fixed in an upper frame. A pressure sensor is mounted between a middle support of the rubber sample and a supporting plate of the vertical compensation device via a first transition column. The synchronization device is mounted between the pressing plate of the vertical compression device and the supporting plate of the vertical compensation device via a second transition column and a cushion block. The transition column penetrates through a hole of the (Continued)

middle support without affecting accuracy of the pressure sensor in a compression stress test with respect to the rubber sample.

17 Claims, 13 Drawing Sheets

(51) Int. Cl.
    *G01N 25/20*     (2006.01)
    *G01K 17/00*     (2006.01)
    *G01N 3/08*     (2006.01)
    *G01N 33/44*     (2006.01)

(56) References Cited

FOREIGN PATENT DOCUMENTS

JP      H7-270294 A      10/1995
JP      H8-285753 A      11/1996

OTHER PUBLICATIONS

Chen, et al., "Gradient Controller Design for Balance Lever of Flexometer", Science Technology and Engineering, vol. 3, No. 13, pp. 780-782 and 805, Jan. 31, 2013.
Wu, et al., "Rubber, Vulcanized-Determination of Temperature Rise and Resistance to Fatigue in Flexometer Testing—Part 2: Compression Flexometer", pp. 182-187, Oct. 1, 1994.

COMPRESSION HEAT-GENERATION DETECTOR AND METHOD THEREFOR

TECHNICAL FIELD

The present invention relates to a compression heat-generation detector and a method therefor, particularly to a device and a method for detecting heat generated under dynamically repeated load or deformation of rubber.

BACKGROUND

Researchers are always interested in heat generated under dynamically repeated load. In practical application, when various kinds of tire and conveyer belts operate in high speed, internal heat, vibration damping, sound insulation materials and their viscoelasticity damping effect of structure are directed to energy loss analysis caused by hysteresis effect of materials.

When a wheel rotates, the tire is repeatedly compressed and deformed due to a load caused by a partial weight of a vehicle and an impact load of a road surface with respect to the wheel. And the work which is consumed by the compression deformation is mostly converted to heat. Since the materials (rubber, a chemical fiber or the like) of most tires are bad thermal conductors, it is hard to diffuse a quantity of heat. Thus, the internal temperature of a tire body increases rapidly. From the test, we came to a conclusion that the internal temperature of the tire is in direct proportion to the product of a load and a speed of the tire. As the speed increases, the load becomes bigger and the temperature increases more rapidly.

The Goodrich's rubber compression heat-generation test machine applies a certain compression load to a sample through an inert-lever system and applies periodic high-frequency compression with specified amplitude to the sample through a transmission system. The compression fatigue temperature rise and fatigue life of the sample are measured under the condition of a room temperature or a temperature higher than the room temperature within a certain period of time. This is applied to vulcanized rubber having a hardness of 30-85 IRHD.

As illustrated in FIG. 1, according to the principle of a conventional compression heat-generator, a distance from a center line of a sample to a lever supporting point 3 is 127±0.5 mm, and a distance from the center line of a load weight 5 to the lever supporting point 3 is 288±0.5 mm. The sample is guided by an upper pressing plate and is reciprocally compressed under the action of the load, and is heated due to the internal resistance of rubber. The compression load to which the sample is subjected adopts an equilibrium compensation principle of a balance lever and uses a lever balance adjusting device 6 to maintain the balance of the lever. The mechanical model is illustrated in FIG. 2. Since a dimension of the sample is changed due to thermal expansion and contraction, or is permanently deformed due to compression during the testing process, the height of the sample is changed. However, the device cannot record the transient changes in the shape, height and dimension of the sample, and cannot transiently control and maintain the constancy of the static force of the preload. The dynamic force is also affected and fluctuates, causing the data to become more inaccurate and unstable and the repeatability becoming relatively poor as the test is performed. Furthermore, a frequency (rotating speed adjustment) of the conventional compression heat-generator and a test temperature are all fixed in a single manner. The dynamic strain of the sample (i.e., a stroke of the upper pressing plate) is also fixed. Accordingly, the compression heat-generation test cannot be performed under the condition of different frequency, temperature and dynamic strain, and it has a single function.

The heat-generator in the current market has several disadvantages as follows.

1. As illustrated in FIG. 3, since the lever supporting point and the sample supporting point are not superimposed on the lower surface of the balance lever equilibrium compensation sample, when the weight difference between the front weight and the back weight causes the lever to be inclined at an angle α, the lower surface of the sample and the upper surface to which the pressure is applied will not be parallel, and it will have a deviation from the model in which the wheels withstand the gravity of a vehicle body and periodically withstand the compression of the vehicle body. Therefore, the actual working condition cannot be accurately simulated under the test condition.

2. The compensation value is not accurate. The compression is in a vertical direction while the compensation is in an inclined direction. Likewise, as illustrated in FIG. 3, the compression applied by the rubber sample is in the vertical direction, while the compensation caused by the lever is in the inclined direction, so that the angle α is formed between compensation direction and vertical compression direction.

3. A central temperature of a core portion cannot be measured in real time. The central temperature of the core portion is actually reflected by a quantity of heat generated by the repeated compression of the rubber material. However, what can be measured in real time in the current market is basically the temperature of the internal environment of the device or a temperature of the sample surface (e.g., bottom). The central temperature of the core portion of the sample can be measured only after stopping a compression test. However, at this time, when a needle-shaped temperature sensor is inserted into the rubber sample, a difference between its temperature and an actual internal temperature of the sample is relatively large. Accordingly, an error occurs in the test result.

4. The device is configured to measure a temperature of only one sample temperature.

5. Some manufacturers can also use a method wherein the internal temperature of a sample can be measured in real time, and usually a temperature measuring wire is inserted by perforating a central position of the sample, or the temperature measuring wire is vulcanized into the central position of the sample when manufacturing the sample. As illustrated in FIG. 4, when the sample is perforated, if the hole is too small, the temperature measuring wire is relatively soft so that it cannot be inserted into the hole. If the hole is too large, the sample may burst during the compression process. At the same time, during the testing process, due to high frequency vibration, deformation of the sample, or the like, the temperature measuring wire may also be separated from the sample and be located off the center position so that the central temperature of the core portion cannot be reflected accurately. When the temperature measuring wire 1 is vulcanized into the test sample, it also cannot be guaranteed that a temperature measuring point is always at the center position of the sample during the vulcanization process.

6. At present, a compression heat-generator manufactured by Ueshima Company in Japan can measure the central temperature of a core portion of a sample in real time. According to a specific method, the device includes one set of temperature sensor inserting units. A needle-shaped temperature sensor can be vertically inserted from the top of a rubber sample into an internal center position of the sample. An inserting depth of the temperature sensor can be controlled by a computer based on feedback information. Before starting the test, the needle-shaped temperature sensor is inserted from the top of the sample into the center position of the sample. During the testing process, a height of the sample is changed according to time and the measured value based on the height changes is fed back to the computer. The inserting position of the needle-shaped temperature sensor can be adjusted to always be located in the center position of the sample by controlling the operation of the temperature sensor inserting unit through the computer. Since this method has a complicated structure and there is a friction phenomenon existing between a probe of the temperature sensor and the rubber sample during the compression process, reliability and operability of the device and accuracy of the test results are affected.

SUMMARY

With respect to the above mentioned problems of the conventional devices, the present invention provides a new compression heat-generation detector and a method therefor to solve the problems according to the conventional art.

The above mentioned compression heat-generation detector includes one set or multi-sets (most preferably, two sets) of detecting units. The detecting unit includes a vertical compression device, a vertical compensation device and a synchronization device for a core portion central temperature sensor. The vertical compression device and the vertical compensation device are respectively fixed to an upper frame. The synchronization device for the core portion central temperature sensor is mounted between a pressing plate of the vertical compression device and a supporting plate of the vertical compensation device via a second transition column, which has the same or similar mechanical properties as a first transition column (most preferably, the same material and diameter as the first transition column), and a cushion block, which has the same or similar mechanical properties as a pressure sensor (most preferably, the same material and shape as a pressure sensor). The second transition column penetrates through a bore of a middle support without affecting an accuracy of the pressure sensor in a compression stress test with respect to a rubber sample. The vertical compression device includes: a compression motor; a stroke adjusting mechanism; a connecting rod; an end connecting member; two long guide shafts; and the pressing plate. The vertical compensation device includes: a compensation motor; two short guide shafts; a lead screw; a lead screw nut; the supporting plate; and the middle support. The synchronization device for the core portion central temperature sensor includes: a core portion central temperature sensor; a lower spring base; an upper spring base; a lower spring; an upper spring; and a sensor fixing ring.

Preferably, the compression heat-generation detector may include a detecting unit in which one set or multi-sets (most preferably, two sets) can be independently driven. A compression heat-generation can be detected with respect to one or a plurality of rubber samples (most preferably, two) simultaneously. Same testing samples (or different testing samples) may be subjected to a comparison test of the compression heat-generation under same testing conditions (or different testing conditions).

In the above solving means, the vertical compression device can compress the rubber sample in a vertical direction.

In the above solving means, the compression motor may press the rubber sample by actuating the pressing plate via the stroke adjusting mechanism, the connecting rod, the end connecting member, and the long guide shafts.

In the above solving means, the stroke adjusting mechanism uses an eccentricity principle (but not limited thereto) and includes bolts, double nuts, a sliding block, and an eccentrically rotating table.

In the above solving means, a vertical compression stroke of the pressing plate is controlled by the stroke adjusting mechanism and the compression stroke can be changed by adjusting the bolts.

In the above solving means, the vertical compensation device can compensate the compression deformation of the rubber sample in the vertical direction.

In the above solving means, a preload which is applied to the rubber sample and a movement of the vertical compensation device are detected and controlled by the pressure sensor. The pressure sensor is mounted between the middle support of the rubber sample and the supporting plate via the first transition column. Applying the preload and the vertical compensation function can be performed by controlling through a magnitude of the detected pressure value.

In the above solving means, the lead screw is directly connected to an output shaft of the compensation motor via a coupler. The supporting plate is directly connected to the lead screw nut and is guided by the two short guide shafts. When the compensation motor is rotated, the lead screw nut and the supporting plate are vertically moved along the two short guide shafts, thereby performing a compensation function.

In the above solving means, a compensation amount of the vertical compensation device is detected and controlled by a displacement sensor and an induction block. The displacement sensor is mounted and fixed to the upper frame. The induction block is mounted to the supporting plate and is moved vertically together with the supporting plate.

In the above solving means, a temperature of a sample room, a bottom temperature of the sample, and a central temperature of a core portion of the sample can be detected simultaneously.

In the above solving means, the temperature of the sample room is measured by a room temperature sensor. The room temperature sensor is mounted within an operating room and is configured to monitor temperature changes in real-time.

In the above solving means, the bottom temperature of the sample is measured by a bottom temperature sensor. The bottom temperature sensor is mounted to the middle support of the sample in an upwardly inclined direction of 45 degrees. A probe of the temperature sensor comes into contact with a bottom of the rubber sample so as to monitor temperature changes at the bottom of the rubber sample in real time during a compression process.

In the above solving means, the core portion central temperature sensor is synchronized and vibrates vertically in accordance with a compression deformation of the rubber sample while a horizontal position is unchanged so that a probe of the core portion central temperature sensor is located at a central position of the rubber sample, thereby monitoring temperature changes of a center of the core portion of the rubber sample in real time during a compression process.

A method of inspecting a sample using the compression heat-generation detector includes: testing changes of a compression deformation, a central temperature of a core portion of the sample, and a bottom temperature of the sample in accordance with compression times during an entire compression process, wherein, when the sample is tested under a constant compression stress so that changes of a compression deformation is measured during a testing process, firstly the pressing plate is disposed on the highest position, the rubber sample having a hole which is previously perforated is put into a sample room having a constant temperature, a probe of the core portion central temperature sensor is located in a central position of the rubber sample, parameters such as magnitudes of a preload, a compression frequency or the like, are set through software, the compensation motor operates after waiting until a temperature is in equilibrium, the supporting plate and the rubber sample are vertically moved upward to generate a compression deformation, a magnitude of a pressure value is detected by the pressure sensor, the compensation motor stops when the pressure value reaches a predetermined preload, the compression motor operates and a compression test is begun, the rubber sample is permanently and constantly compressed as compression is performed so that a minimum pressure value, i.e., the preload, detected by the pressure sensor during the compression becomes smaller, at this time, a vertical compensation movement is performed by controlling an operation of the compensation motor until the preload returns back to the predetermined value, a compensation amount can be acquired by a feedback of a displacement sensor and an induction block; and testing changes of a compression stress, a central temperature of a core portion of the sample, and a bottom temperature of the sample in accordance with compression times if the same compression deformation occurs in the sample, wherein, when the sample is tested under a constant compression deformation so that changes of a compression stress is measured during a testing process, firstly the pressing plate is disposed on the highest position, the rubber sample having a hole which is previously perforated is put into a sample room having constant temperature, a probe of the core portion central temperature sensor is located in a central position of the rubber sample, parameters, such as predetermined magnitudes of a deformation, a compression frequency or the like, are set through software, the compensation motor operates after waiting until a temperature is in equilibrium, the supporting plate and the rubber sample are vertically moved upward to generate a compression deformation, the compensation motor stops when it reaches a predetermined amount of the compression deformation, the compression motor operates and a compression test is begun, the rubber sample is permanently and constantly compressed as compression is performed so that the compression stress detected by the pressure sensor becomes gradually smaller.

The compression heat-generation detector according to the present invention has the advantages as follows.

(1) Compression in the Vertical Direction

As illustrated in FIG. 9, the output shaft of the compression motor is connected to two guide shafts through one stroke adjusting mechanism, the connecting rod and the end connecting member. The motor starts to guide and move the guide shaft vertically. Accordingly, the pressing plate reciprocates vertically so that the rubber sample is compressed. A compression load is detected by the pressure sensor.

(2) Compensation in the Vertical Direction

After testing for certain time periods, the rubber testing sample is permanently compressed and deformed. In order to ensure accuracy of test data, the permanent compression deformation is compensated using the compensation motor and the lead screw structure. Its structural principle is illustrated in FIGS. 5 and 11. The rubber sample is connected to the lead screw nut via the middle support, the transition column, the pressure sensor and the supporting plate. When the compensation motor moves the lead screw via the coupler, the rubber sample is driven via the lead screw nut and the supporting plate so as to make a very little offset in the vertical direction. Accordingly, the permanent deformation amount of the rubber sample is compensated.

Since the compression direction and the compensation direction of the rubber sample are always vertical, the lower surface of the sample and the upper surface to which the pressure is applied are always parallel. Thus, it is possible to simulate the actual working condition precisely.

(3) The central temperature of the core portion and the bottom temperature of the sample can be detected simultaneously. A location of the temperature sensor is illustrated in FIG. 9.

The synchronization device for the core portion central temperature sensor includes: the core portion central temperature sensor, the lower spring base, the upper spring top base, the lower spring, the upper spring, and the sensor fixing ring. The entire synchronization device is mounted between the pressing plate of the vertical compression device and the supporting plate of the vertical compensation device via a second transition column which has the same or similar mechanical properties as a first transition column (most preferably, the same material and diameter as the first transition column) and the cushion block which has the same or similar mechanical properties as the pressure sensor (most preferably, the same material and shape as the pressure sensor). The second transition column penetrates through the bore of the middle support without affecting the accuracy of the pressure sensor in a compression stress test with respect to the rubber sample.

When the height of the entire spring synchronization device is equal to the height of the upper and lower thermal insulation plate and the rubber sample is compressed and deformed, the upper spring is deformed equally to the lower spring. The temperature sensor which is located at the center of the spring synchronization device is always positioned at the center of the rubber sample. The temperature sensor is connected and fixed to the sensor fixing ring by the threaded portion. During the compression process, the horizontal direction is unchanged. Therefore, although the rubber sample is deformed anyhow during the entire testing process, the endpoint of the core portion central temperature sensor is always located at the center of the rubber sample. Its structural principle is illustrated in FIG. 12.

The bottom temperature sensor is fixed to the middle support of the rubber sample in an upwardly inclined direction of 45 degrees by the threaded portion. The corresponding positions of the lower thermal insulation plate and the lower pressing plate are perforated. The probe of the bottom temperature sensor protrudes to come into direct contact with the bottom of the rubber sample. Accordingly, it is possible to monitor the temperature changes at the bottom of the rubber sample in real time during the compression process. Its structural principle is illustrated in FIG. 14.

DETAILED DESCRIPTION

The present invention includes one set or multi-sets (most preferably, two sets) of detecting units which are independently driven. Each independent detecting unit includes one set of vertical compression devices, one set of vertical compensation devices, and a synchronization device for a core portion central temperature sensor.

Figure 6:
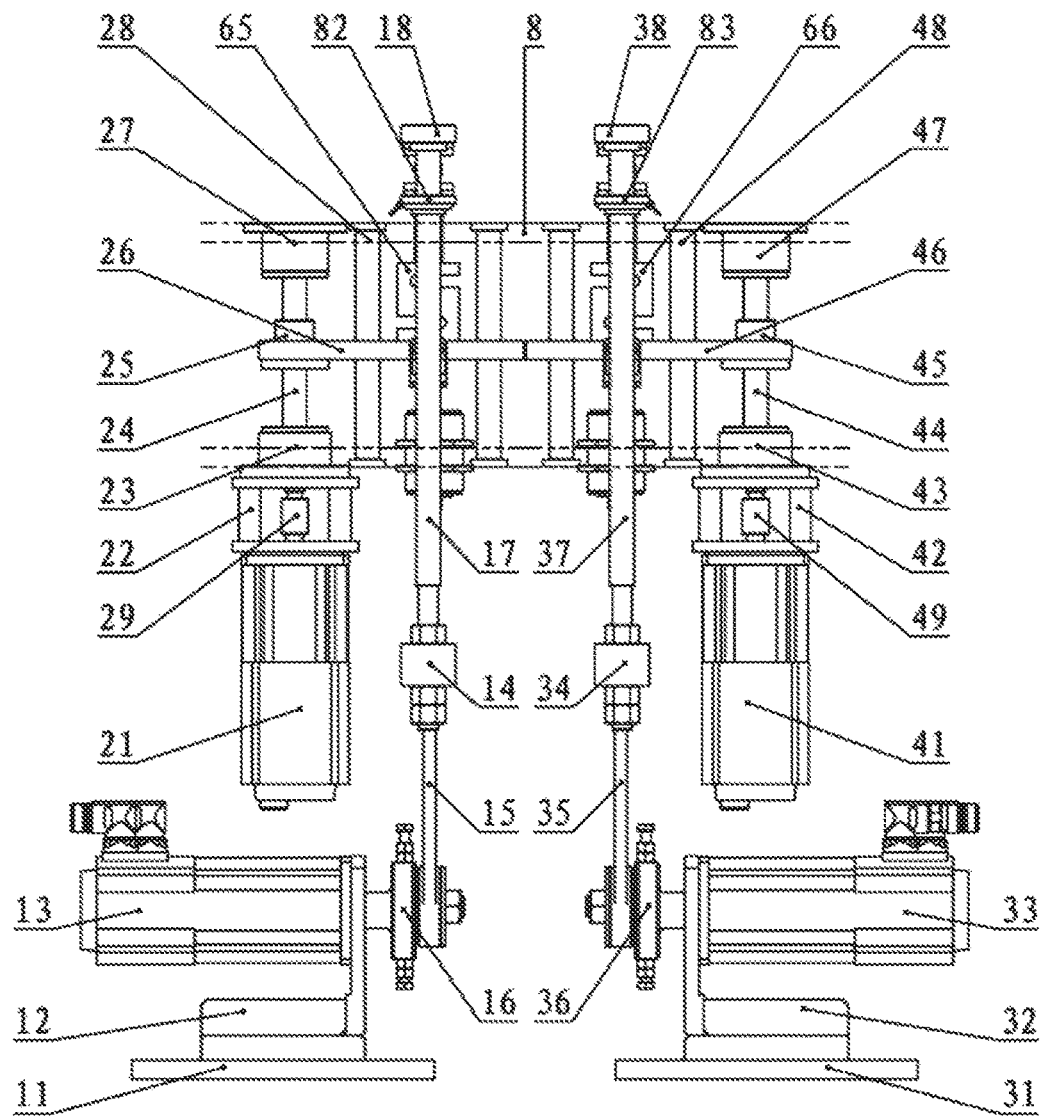
FIG. 6 is a front view illustrating the compression heat-generation detector according to the present invention.
Figure 7:
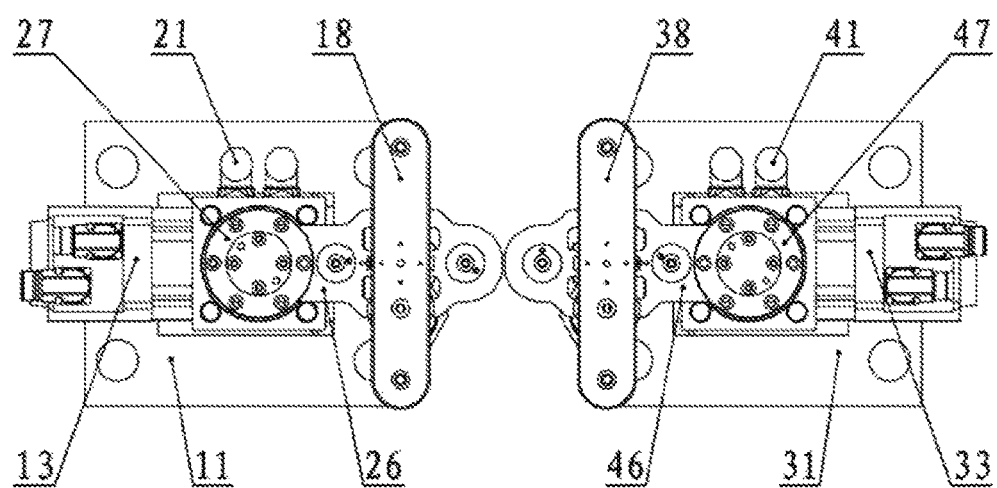
FIG. 7 is a top view illustrating the compression heat-generation detector according to the present invention.
Figure 8:
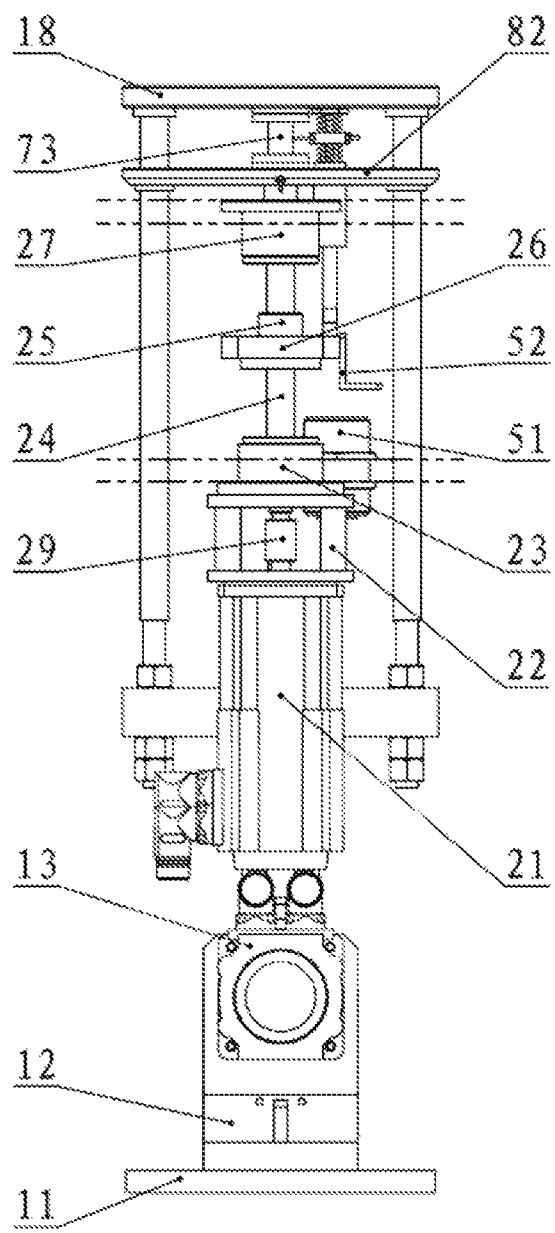
FIG. 8 is a left side view illustrating the compression heat-generation detector according to the present invention.

As illustrated in FIG. 6, in an example of one set of the detecting units, the vertical compression device and the vertical compensation device are respectively fixed to an upper frame 8. A long guide shaft 17 of the vertical compression device is vertically guided along a corresponding bore of the upper frame 8. A lead screw lower bearing box 23 and an upper bearing box 27 in the vertical compensation device are respectively fixed to the upper frame 8. Likewise, two short guide shafts 28 are also fixed to the upper frame 8. The synchronization device for the core portion central temperature sensor is mounted between a pressing plate 18 of the vertical compression device and a supporting plate 26 of the vertical compensation device.

As illustrated in FIGS. 5 to 9, for example, one set of the vertical compression devices includes a base 11, a compression motor bracket 12, a compression motor 13, an end connecting member 14, a connecting rod 15, a stroke adjusting mechanism 16, the long guide shaft 17, the pressing plate 18, or the like. Among the above, the compression motor 13 is mounted to the compression motor bracket 12 and fixed to the base 11. An output shaft of the compression motor 13 is connected to the end connecting member 14 via the stroke adjusting mechanism 16 and the connecting rod 15. Both ends of the long guide shaft 17 are connected to the end connecting member 14 and the pressing plate 18, respectively. When the compression motor starts to rotate, the long guide shaft 17 reciprocates vertically to actuate the pressing plate 18 so that a rubber sample is compressed.

As illustrated in FIGS. 5 to 8, for example, one set of the vertical compensation devices includes a compensation motor 21, a compensation motor bracket 22, the lead screw lower bearing box 23, a lead screw 24, a lead screw nut 25, a supporting plate 26, a lead screw upper bearing box 27, the short guide shafts 28, a coupler 29, or the like. Among the above, the compensation motor 21 is fixed to the upper frame 8 of the device via the compensation motor bracket 22. An output shaft of the compensation motor is directly connected to the lead screw 24 via the coupler 29. The lead screw nut 25 is connected to the supporting plate 26 and guided vertically by the two short guide shafts 28. When the compensation motor 21 starts to rotate, the lead screw 24 is rotated to move the supporting plate 26 vertically and linearly by actuation of the lead screw 24 so that a compression deformation of the rubber sample 73 is compensated. A compensation amount of the vertical compensation device is detected and controlled by a displacement sensor 51 and an induction block 52. The displacement sensor 51 is mounted and fixed to the upper frame 8. The induction block 52 is mounted to the supporting plate 26 and is movable vertically together with the supporting plate 26. In the present invention, a structure of a ball lead screw and a lead screw nut is used, but a function of a vertical compensation can be realized by using a general screw and nut.

Figure 9:
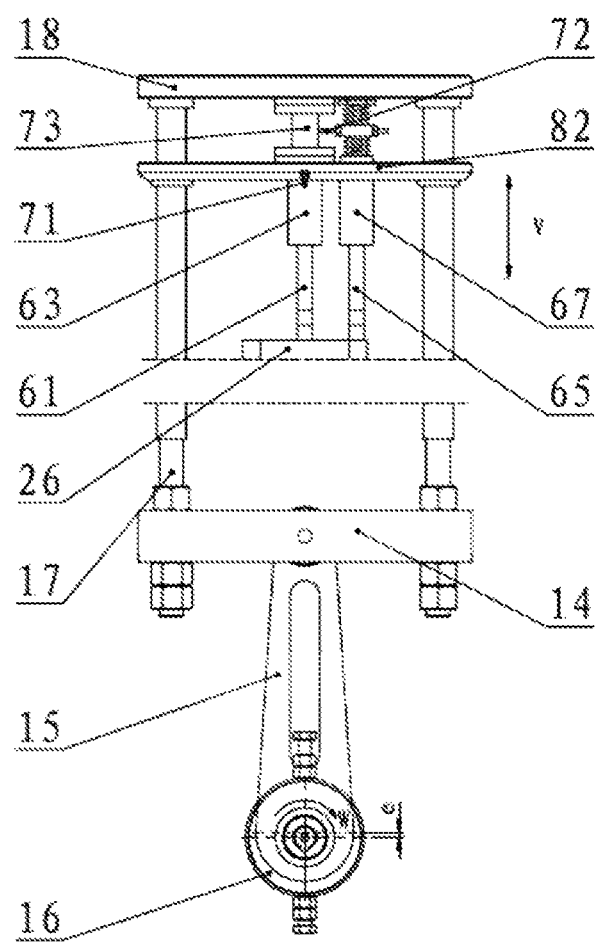
FIG. 9 is a view illustrating an operation principle of a vertical compression in the compression heat-generation detector according to the present invention.

As illustrated in FIG. 9, the pressing plate 18 reciprocates vertically together with the long guide shaft 17 so that a high frequency compression with respect to the rubber sample 73 can be performed. A compression stroke of the pressing plate 18 is directly determined by an eccentric distance "e" of the stroke adjusting mechanism 16 and the relationship therebetween is as follows: compression stroke=2e. Thus, the compression stroke of the pressing plate 18 can be adjusted by changing the eccentric distance "e" of the stroke adjusting mechanism 16.

Figure 10:
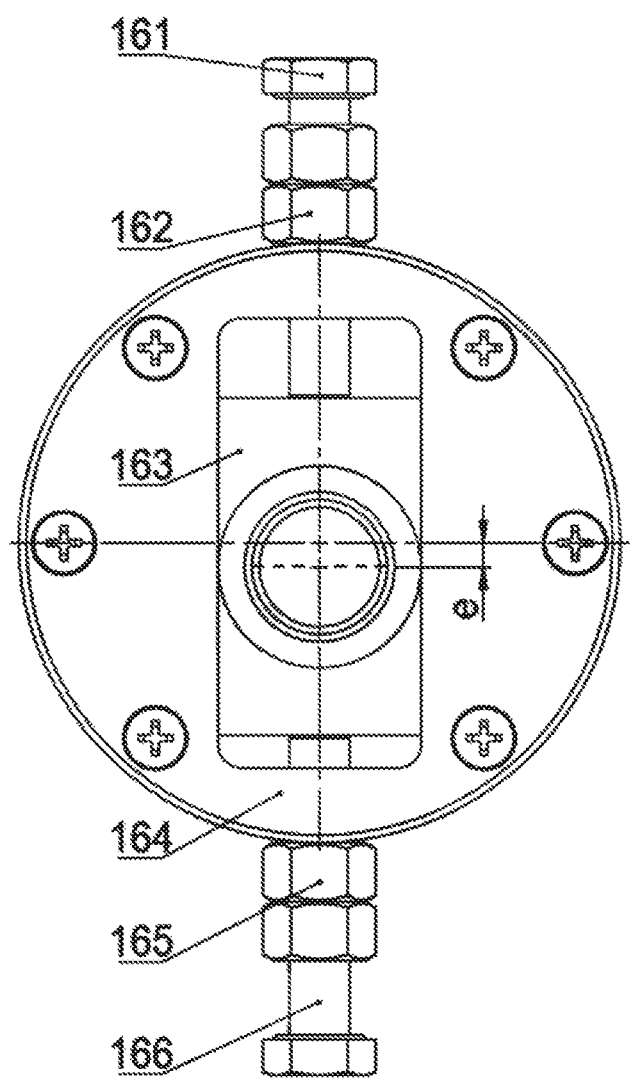
FIG. 10 is a view illustrating an operation principle of a stroke adjustment in the compression heat-generation detector according to the present invention.

FIG. 10 is a view illustrating an adjustment principle of the eccentric distance "e" of the stroke adjusting mechanism 16. The stroke adjusting mechanism 16 includes bolts 161 and 166, double nuts 162 and 165, a sliding block 163, and an eccentrically rotating table 164. By adjusting the bolts 161 and 166, the sliding block 163 is slidable within the eccentrically rotating table 164 to thereby form a certain amount of the eccentric distance "e". After the eccentric distance "e" is adjusted, the eccentric distance "e" is fixed by fastening the double nuts 162 and 165 so that a change of the eccentric distance "e" caused by a vibration can be effectively prevented.

Figure 1:
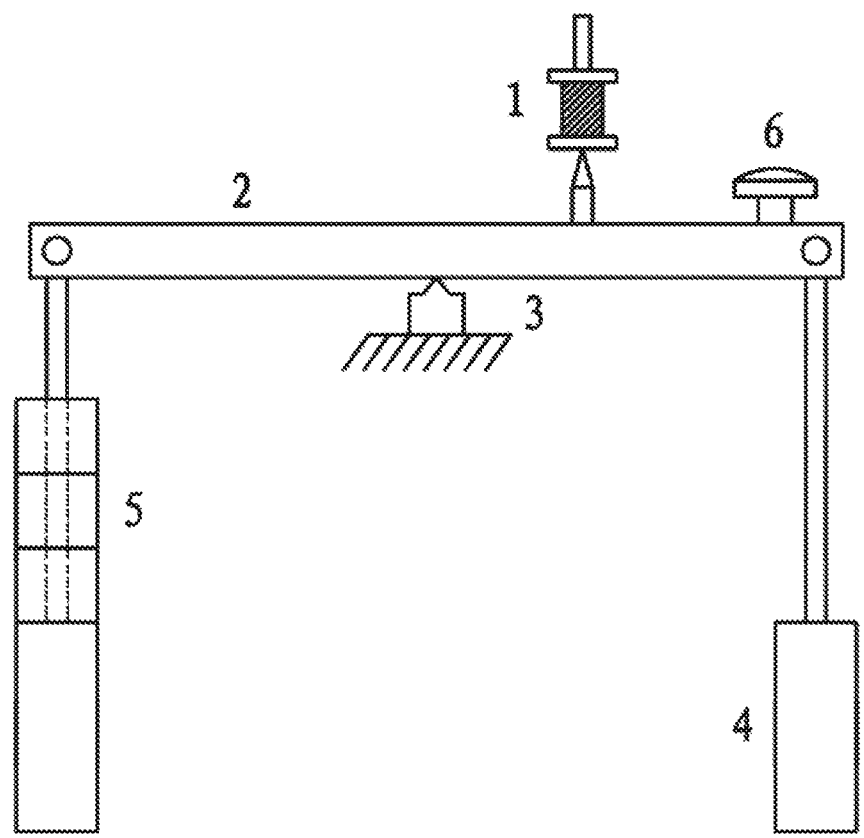
FIG. 1 is a view illustrating an operation principle of a conventional compression heat-generator.
Figure 2:
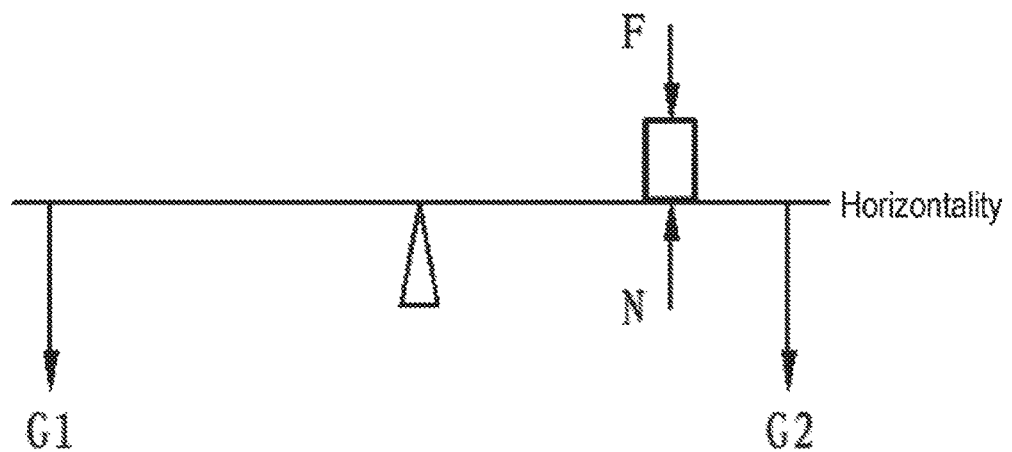
FIG. 2 is a mechanical model of the conventional compression heat-generator.
Figure 3:
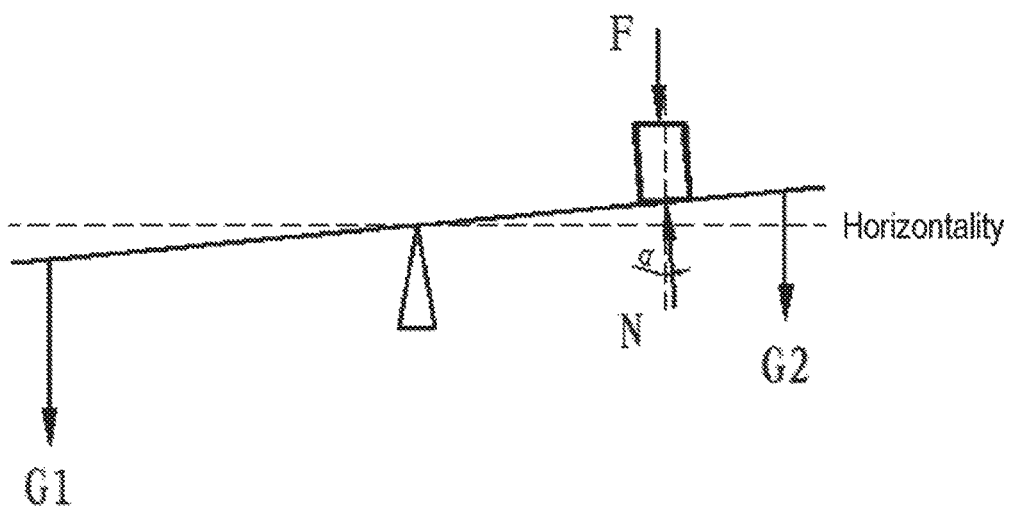
FIG. 3 is a schematic view illustrating that upper and lower surfaces of a sample are not parallel.
Figure 4A:
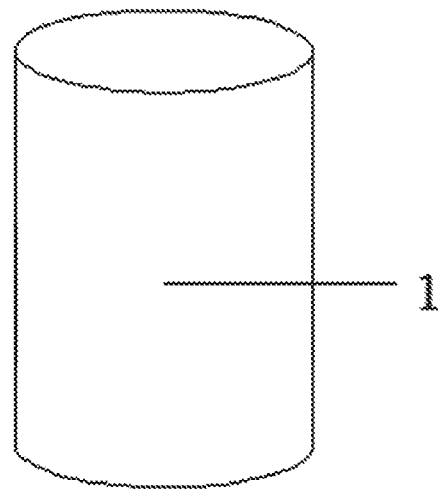
FIG. 4 is a schematic view illustrating a positional change of a temperature measuring wire.
Figure 4B:
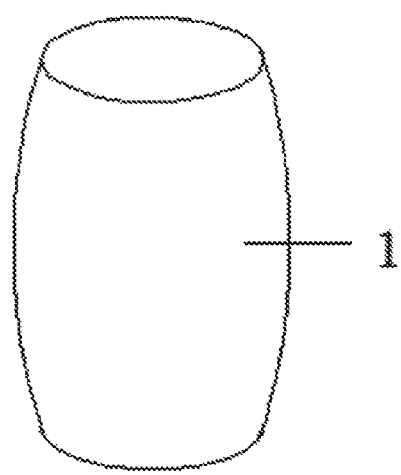
Figure 5:
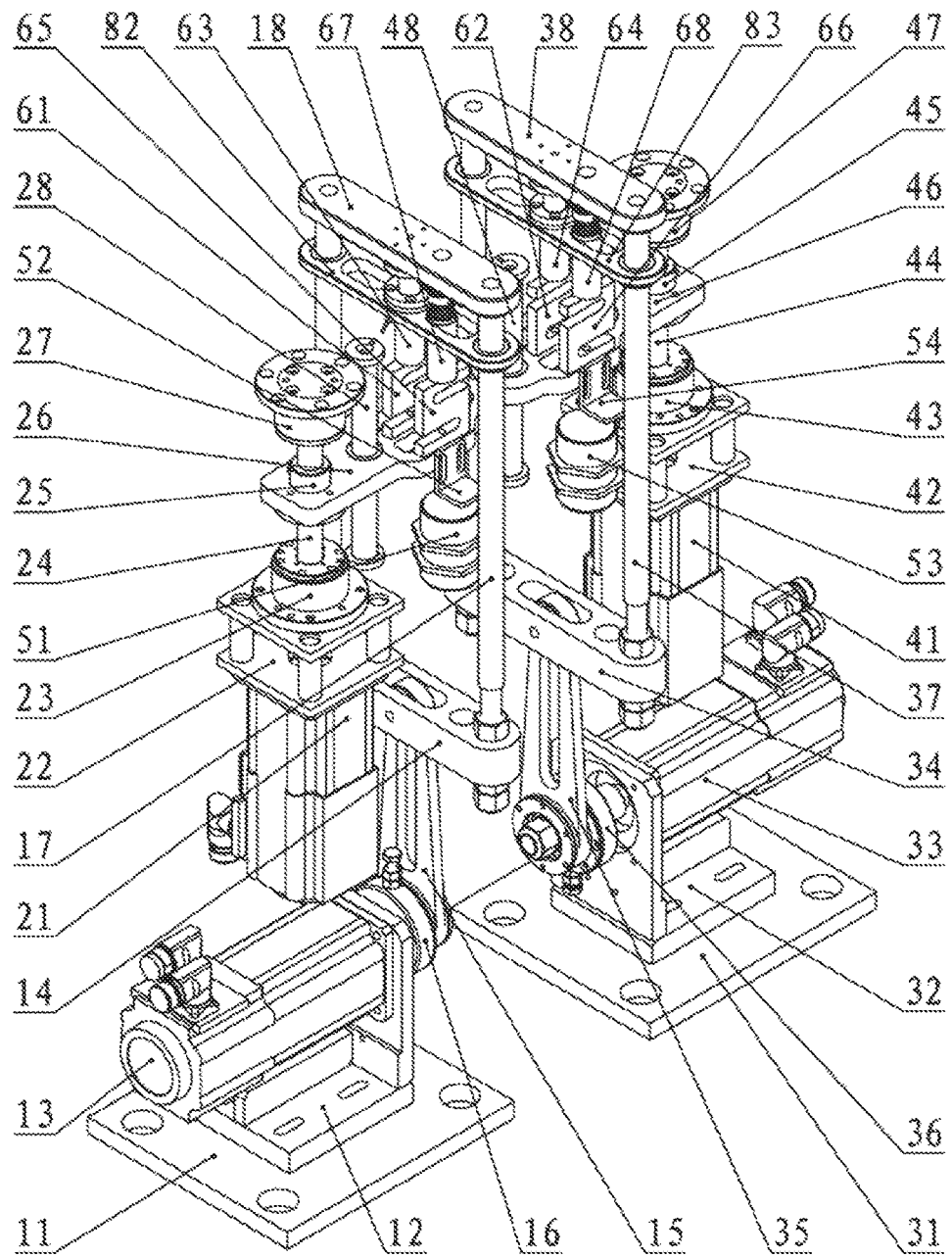
FIG. 5 is a perspective view illustrating a compression heat-generation detector according to the present invention.
Figure 11:
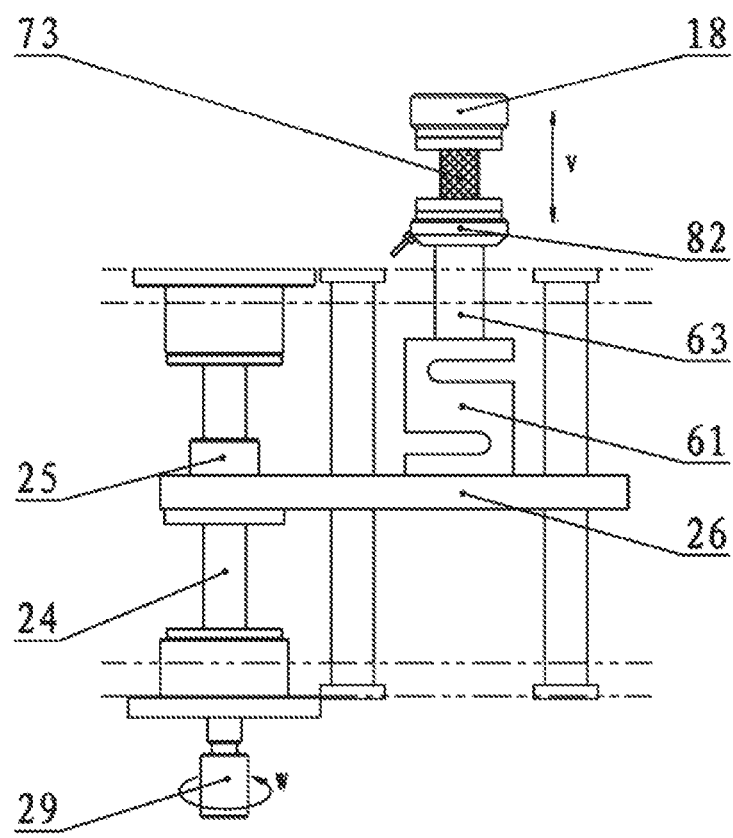
FIG. 11 is a view illustrating an operation principle of a vertical compensation in the compression heat-generation detector according to the present invention.

As illustrated in FIGS. 5 and 11, a pressure sensor 61 is mounted between a middle support 82 of the rubber sample and the supporting plate 26 via a transition column 63. Before testing, the pressing plate 18 is disposed on the highest position, the supporting plate 26, the middle support 82 of the rubber sample and the rubber sample 73 is moved upwardly by the compensation motor 21 after setting a preload. Then, the rubber sample 72 is compressed to be deformed and the preload is applied. A magnitude of a preload value is detected by the pressure sensor 61. After the preload value reaches a predetermined preload, the compensation motor 21 stops, the compression motor 13 operates, and the rubber sample 73 begins to be compressed. During an entire high frequency compression process, the pressing plate 18 and the rubber sample 73 are always in contact with each other and are not separated. Thus, a pressure value detected by the pressure sensor 61 fluctuates in a form of a wave. The lowest point value of the wave is the preload value. After the rubber sample 73 is permanently compressed and deformed, the minimum pressure value (i.e., the preload value) detected by the pressure sensor 61 becomes smaller since the compression stroke of the pressing plate 18 is not changed. At this time, the supporting plate 26 is moved upward by controlling an operation of the compensation motor 21 so that a permanent compression deformation caused in the rubber sample 73 is compensated. When the preload value returns back to the initially predetermined value, the compensation motor 21 stops and a first compensation operation is completed. A compensation amount is acquired by the displacement sensor 51 and the induction block 52.

Figure 12:
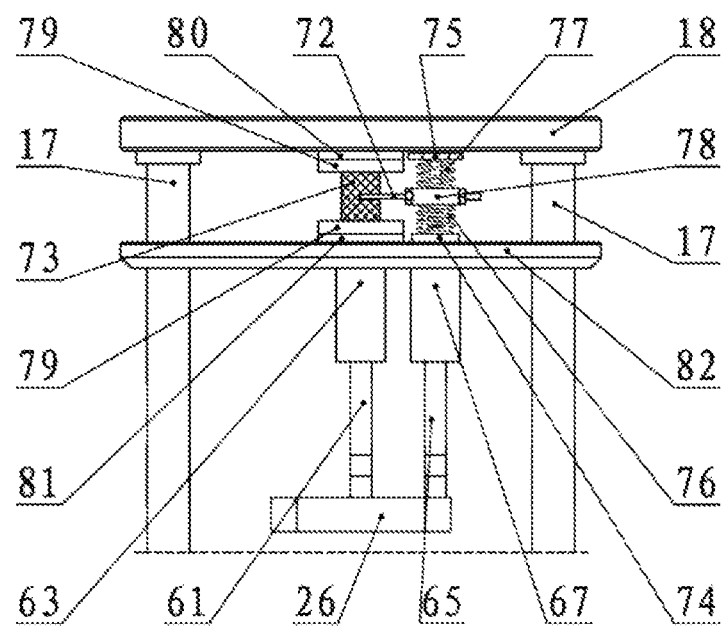
FIG. 12 is a structural schematic view illustrating a synchronization device for a core portion central temperature sensor in the compression heat-generation detector according to the present invention.
Figure 13:
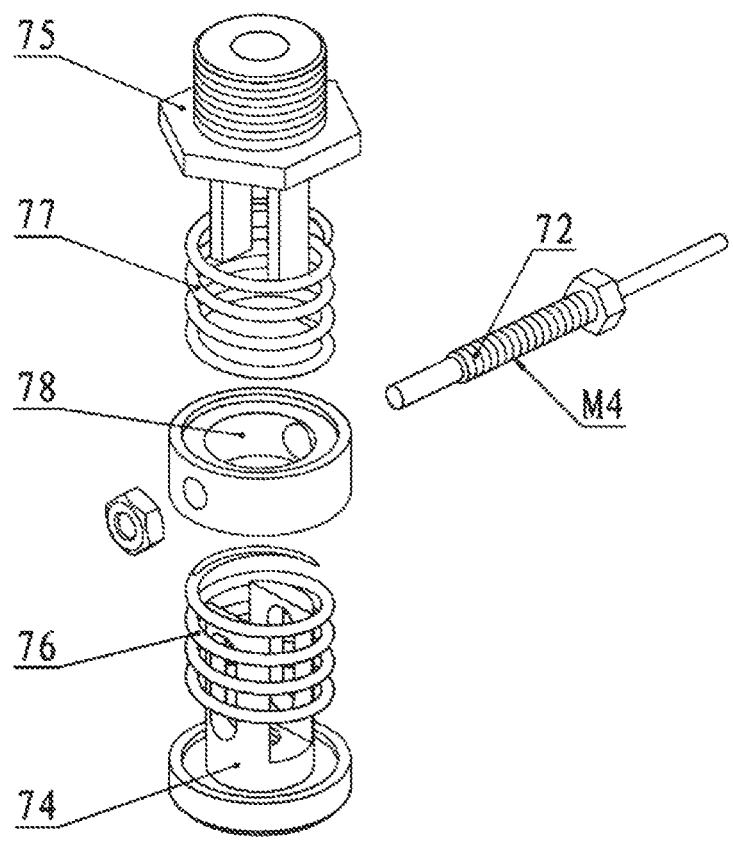
FIG. 13 is an exploded schematic view illustrating the synchronization device for the core portion central temperature sensor in the compression heat-generation detector according to the present invention.

FIG. 12 illustrates the synchronization device for the core portion central temperature sensor that includes a core portion central temperature sensor 72, a lower spring base 74, an upper spring base 75, a lower spring 76, an upper spring 77, and a sensor fixing ring 78. An exploded schematic view of this structure is illustrated in FIG. 13. Before a compression test begins, the rubber sample 73 is perforated along a central position. A probe portion of the core portion central temperature sensor 72 is inserted into a central hole of the rubber sample 73 so that the central temperature of the core portion of the rubber sample 73 can be measured. In this synchronization device, the upper spring 77 is exactly the same as the lower spring 76. This ensures that the compression deformation of both upper and lower springs is exactly the same as each other during a compression vibration process. Accordingly, the sensor fixing ring 78 and the sensor 72 are always located at the vertically central position of the rubber sample 73. The sensor fixing ring 78 is positioned installed outside a cylindrical portion of guide arms of the upper spring base 75 and the lower spring base 74. The core portion central temperature sensor has an M4 male thread at the distal end thereof. The M4 male thread penetrates through the lower spring base 74 and the sensor fixing ring 78 to be fastened by one M4 nut. Accordingly, it is possible to prevent the core portion central temperature sensor from causing a vertical offset during the compression vibration process, thereby always detecting the central temperature of the core portion of the rubber sample 73.

The synchronization device for the core portion central temperature sensor is mounted between the pressing plate 18 of the vertical compression device and the supporting plate 26 of the vertical compensation device via a transition column 67 which has the same or similar mechanical properties as the transition column 63 (most preferably, the same material and diameter as the transition column 63) and a cushion block 65 which has the same or similar mechanical properties as the pressure sensor 61 (most preferably, the same material and shape as the pressure sensor 61). A bottom of the lower spring base 74 and a bottom of a lower thermal insulation plate 81 are located in the same horizontal plane. When the supporting plate 26 is vertically moved, the deformation of the upper and lower springs 77 and 16 is completely synchronized with the deformation of the rubber sample 73. The transition column 67 penetrates through the bore of the middle support 82 without affecting accuracy of the pressure sensor 61 in a compression stress test with respect to the rubber sample 73.

During the compression process, if the rubber sample 73 comes into contact with metal (or other materials having a good thermal conductivity), a quantity of heat generated by the compression is transmitted to the outside to affect test results. Thus, in the present invention, the thermal insulation plates 80 and 81 are configured to have good thermal insulation performance and are made of materials with high hardness (for example, including phenolic resin materials but not limited thereto). The thermal insulation plates 80 and 81 have high hardness without affecting a compression amount, and also have good thermal resistance without affecting a temperature measurement.

Figure 14:
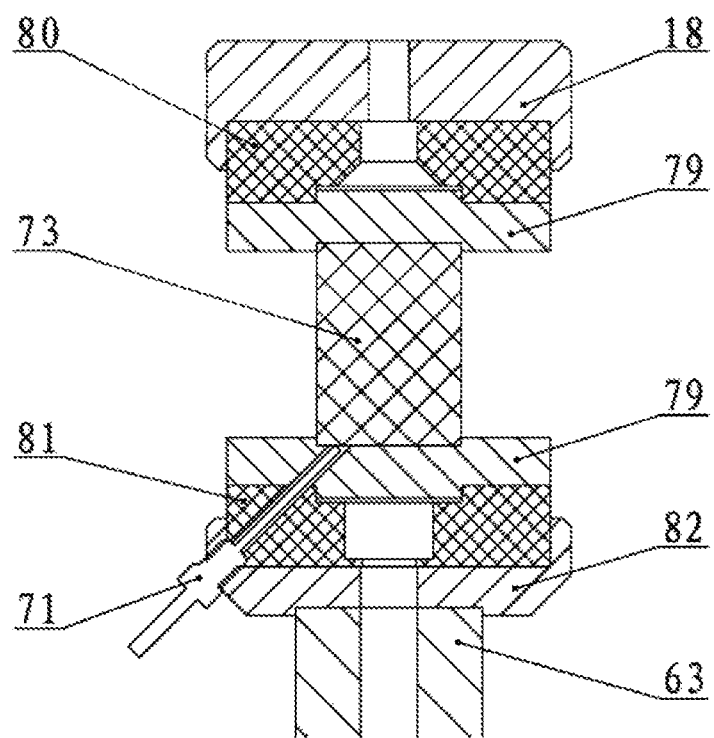
FIG. 14 is a sectional schematic view illustrating a bottom temperature sensor in the compression heat-generation detector according to the present invention.

As illustrated in FIG. 9, the bottom temperature sensor 71 is connected and fixed to the middle support 82 of the rubber sample in an upwardly inclined direction of 45 degrees by a threaded portion. A sectional view related to the detailed position is illustrated in FIG. 14. An M4 inner threaded hole is designed in a corresponding position of the middle support 82 of the rubber sample. One long and narrow hole is designed in a corresponding position of the lower thermal insulation plate 81 and the lower pressing plate 79. When the bottom temperature sensor 71 is fixed to the middle support 82 of the rubber sample via the threaded portion, the probe of the bottom temperature sensor penetrates through the long and narrow hole of the lower thermal insulation plate 81 and the lower pressing plate 79, thereby coming into contact with the bottom of the rubber sample. Accordingly, it is possible to monitor temperature changes at the bottom of the rubber sample in real time during the compression process. Among the above, as illustrated in FIG. 13, the structure of the bottom temperature sensor is similar to the structure of the core portion central temperature sensor.

What is claimed is:

1. A compression heat-generation detector, comprising:
one or more sets of detecting units,
wherein each of the detecting units includes a vertical compression device, a vertical compensation device and a synchronization device for a core portion central temperature sensor,
wherein the vertical compression device and the vertical compensation device are fixed to an upper frame, respectively,
wherein a first transition column is disposed between a pressing plate of the vertical compression device and a pressure sensor, and penetrates through a bore of a middle support,
wherein the synchronization device for the core portion central temperature sensor is mounted between the pressing plate of the vertical compression device and a supporting plate of the vertical compensation device via a second transition column which has the same or similar mechanical properties as the first transition column and a cushion block which has the same or similar mechanical properties as the pressure sensor,
wherein the second transition column is disposed between the pressing plate and the cushion block, and penetrates through the bore of the middle support without affecting accuracy of the pressure sensor in a compression stress test with respect to at least one rubber sample which is disposed between the pressing plate and the middle support,
wherein the vertical compression device includes a compression motor, a stroke adjusting mechanism, a connecting rod, an end connecting member, two long guide shafts, and the pressing plate,
wherein the vertical compensation device includes a compensation motor, two short guide shafts, a lead screw, a lead screw nut, the supporting plate, and the middle support, and
wherein the synchronization device for the core portion central temperature sensor includes the core portion central temperature sensor, a lower spring base, an upper spring base, a lower spring, an upper spring, and a sensor fixing ring.

2. The compression heat-generation detector according to claim 1, wherein each of the one or more sets of detecting units can be independently driven,
wherein the at least one rubber sample includes a plurality of rubber samples,
wherein a compression heat-generation can be detected with respect to the plurality of rubber samples simultaneously, and
wherein same testing samples or different testing samples are subjected to a comparison test of the compression heat-generation under same testing conditions or different testing conditions.

3. The compression heat-generation detector according to claim 1, wherein a material and a diameter of the second transition column are the same as those of the first transition column.

4. The compression heat-generation detector according to claim 1, wherein a material and a shape of the cushion block are the same as those of the pressure sensor.

5. The compression heat-generation detector according to claim 1, wherein the compression motor presses the rubber sample by actuating the pressing plate via the stroke adjusting mechanism, the connecting rod, the end connecting member and the long guide shafts.

6. The compression heat-generation detector according to claim 1, wherein the vertical compensation device can compensate a compression deformation or a compression stress of the rubber sample in a vertical direction, such that the compression deformation and compression stress of the rubber sample can be measured at the same time during a testing process,
wherein the sample is tested under a constant compression stress so that changes of the compression deformation can be measured during the testing process, and
wherein the sample is tested under a constant compression deformation so that changes of the compression stress can be measured during the testing process.

7. A method of inspecting a sample using the compression heat-generation detector according to claim 1, comprising:
testing changes of a compression deformation, a central temperature of a core portion of the sample, and a bottom temperature of the sample in accordance with compression times during an entire compression process, wherein, when the sample is tested under a constant compression stress so that changes of a compression deformation is measured during a testing process, firstly the pressing plate is disposed on the highest position, the sample having a hole which is previously perforated is put into a sample room having a constant temperature, a probe of the core portion central temperature sensor is located in a central position of the sample, parameters including magnitudes of a preload and a compression frequency are set through software, the compensation motor operates after waiting until a temperature is in equilibrium, the supporting plate and the sample are vertically moved upward to generate a compression deformation, a magnitude of a pressure value is detected by the pressure sensor, the compensation motor stops when the pressure value reaches a predetermined preload, the compression motor operates and a compression test is begun, the sample is permanently and constantly compressed as compression is performed so that a minimum pressure value, detected by the pressure sensor during the compression, becomes smaller, a vertical compensation movement is performed by controlling an operation of the compensation motor until the preload returns back to the predetermined value, a compensation amount can be acquired by a feedback of a displacement sensor and an induction block; and
testing changes of a compression stress, a central temperature of a core portion of the sample, and a bottom temperature of the sample in accordance with compression times if the same compression deformation occurs in the sample, wherein, when the sample is tested under a constant compression deformation so that changes of a compression stress is measured during a testing process, firstly the pressing plate is disposed on the highest position, the sample having a hole which is previously perforated is put into the sample room having the constant temperature, a probe of the core portion central temperature sensor is located in a central position of the sample, parameters including predetermined magnitudes of a deformation and a compression frequency are set through software, the compensation motor operates after waiting until a temperature is in equilibrium, the supporting plate and the sample are vertically moved upward to generate a compression deformation, the compensation motor stops when it reaches a predetermined amount of the compression deformation, the compression motor operates and a compression test is begun, the sample is permanently and constantly compressed as compression is performed so that the compression stress detected by the pressure sensor becomes gradually smaller.

8. The compression heat-generation detector according to claim 1, wherein the one or more sets of detecting units include two sets of detecting units.

9. The compression heat-generation detector according to claim 8, wherein the at least one rubber sample includes two rubber samples, and
wherein the two rubber samples are disposed between the pressing plate and the middle support.

10. The compression heat-generation detector according to claim 1, wherein the stroke adjusting mechanism uses an eccentricity principle and includes bolts, double nuts, a sliding block and an eccentrically rotating table.

11. The compression heat-generation detector according to claim 10, wherein a vertical compression stroke of the pressing plate is controlled by the stroke adjusting mechanism and the compression stroke can be changed by adjusting the bolts.

12. The compression heat-generation detector according to claim 1, wherein the lead screw is directly connected to an output shaft of the compensation motor via a coupler,
wherein the supporting plate is directly connected to the lead screw nut and is guided by the two short guide shafts, and
wherein, when the compensation motor is rotated, the lead screw nut and the supporting plate are vertically moved along the two short guide shafts, thereby performing a compensation function.

13. The compression heat-generation detector according to claim 12, wherein a preload which is applied to the rubber sample and a movement of the vertical compensation device is detected and controlled by the pressure sensor,
wherein the pressure sensor is mounted between the middle support of the rubber sample and the supporting plate via the first transition column,
wherein when the sample is tested under a constant compression stress so that changes of a compression deformation is measured during a testing process, if the rubber sample is permanently compressed and deformed as the testing process is performed, the compression stress detected by the pressure sensor becomes smaller, wherein, at this time, controlling an operation of the compensation motor and compensating the compression deformation in the vertical direction ensures that the compression stress is unchanged, wherein a vertical compensation amount of the compression deformation of the rubber sample is detected by a displacement sensor and an induction block, and wherein when the sample is tested under a constant compression deformation so that changes of a compression stress is measured during the testing process, an amount of the compression deformation is detected and controlled by the displacement sensor and the induction block and the compression stress is detected by the pressure sensor.

14. The compression heat-generation detector according to claim 1, wherein a temperature of a sample room, a bottom temperature of the sample and a central temperature of a core portion of the sample can be detected simultaneously.

15. The compression heat-generation detector according to claim 14, wherein the temperature of the sample room is measured by a room temperature sensor, and wherein the room temperature sensor is mounted within an operating room and is configured to monitor temperature changes in real-time.

16. The compression heat-generation detector according to claim 14, wherein the bottom temperature of the sample is measured by a bottom temperature sensor, wherein the bottom temperature sensor is mounted to the middle support of the rubber sample in an upwardly inclined direction of 45 degrees, wherein a probe of the temperature sensor comes into contact with a bottom of the rubber sample so as to monitor temperature changes at the bottom of the rubber sample in real time during a compression process.

17. The compression heat-generation detector according to claim 14, wherein the core portion central temperature sensor is synchronized and vibrates vertically in accordance with a compression deformation of the rubber sample while a horizontal position is unchanged so that a probe of the core portion central temperature sensor is located at a central position of the rubber sample, thereby monitoring temperature changes of a center of the core portion of the rubber sample in real time during a compression process.

* * * * *